(12) United States Patent
DeLegge

(10) Patent No.: US 7,547,303 B2
(45) Date of Patent: Jun. 16, 2009

(54) CATHETER ASSEMBLY INCLUDING FOLDABLE INTERNAL BOLSTER

(75) Inventor: Rebecca DeLegge, Mt. Pleasant, SC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/499,228

(22) Filed: Aug. 3, 2006

(65) Prior Publication Data

US 2008/0097392 A1    Apr. 24, 2008

(51) Int. Cl.
*A61M 25/04* (2006.01)
(52) U.S. Cl. .................. 604/523; 604/104; 604/108; 604/910; 604/264; 604/285
(58) Field of Classification Search .................. 604/104, 604/106, 107, 544, 910, 385, 325, 385.28, 604/95.03, 103.04, 95.01, 264, 271, 523, 604/284
See application file for complete search history.

(56) References Cited

U.S. PATENT DOCUMENTS

| | | | |
|---|---|---|---|
| 4,740,195 A * | 4/1988 | Lanciano | 604/533 |
| 4,861,334 A | 8/1989 | Nawaz | |
| 4,863,438 A | 9/1989 | Gauderer | |
| 4,900,306 A | 2/1990 | Quinn et al. | |
| 4,944,732 A | 7/1990 | Russo | |
| 5,112,310 A | 5/1992 | Grobe | |
| 5,167,627 A | 12/1992 | Clegg et al. | |
| 5,391,159 A | 2/1995 | Hirsch et al. | |
| 5,489,269 A | 2/1996 | Aldrich et al. | |
| 5,720,734 A | 2/1998 | Copenhaver et al. | |
| 5,730,724 A * | 3/1998 | Plishka et al. | 604/95.04 |
| 5,836,924 A | 11/1998 | Kelliher et al. | |
| 6,042,577 A | 3/2000 | Chu et al. | |

(Continued)

FOREIGN PATENT DOCUMENTS

DE    195 43 713 A1    5/1996

(Continued)

*Primary Examiner*—Nicholas D Lucchesi
*Assistant Examiner*—Quynh-Nhu H Vu
(74) *Attorney, Agent, or Firm*—Kriegsman & Kriegsman

(57) ABSTRACT

A catheter assembly including a foldable internal bolster. According to one embodiment, the catheter assembly includes a catheter, a first flexible filament and a second flexible filament. The catheter includes a tubular body and a pair of flexible legs. The tubular body is a generally cylindrical member shaped to include a proximal end, a distal end, a longitudinal lumen, a pair of external notches, a first bore extending from the proximal end to one of the notches, and a second bore extending from the proximal end to the other of the notches. Each of the flexible legs has a fixed end and a free end, the fixed end being integrally formed on the distal end of the tubular body. One end of the first filament is fixed to one of the flexible legs, and the opposite end of the first filament is slidably inserted up through the first bore. One end of the second filament is fixed to the other of the flexible legs, and the opposite end of the second filament is slidably inserted up through the second bore. Consequently, by pulling the filaments up through their respective bores, the free ends of the legs may be drawn towards the tubular body to form a pair of loops suitable for use as an internal bolster.

21 Claims, 8 Drawing Sheets

U.S. PATENT DOCUMENTS

| | | | |
|---|---|---|---|
| 6,315,789 B1 * | 11/2001 | Cragg | 606/232 |
| 6,558,349 B1 | 5/2003 | Kirkman | |
| 6,929,621 B2 * | 8/2005 | Whitmore et al. | 604/109 |
| 2004/0068252 A1 | 4/2004 | Whitmore et al. | |

FOREIGN PATENT DOCUMENTS

| | | |
|---|---|---|
| WO | WO 03/092780 A2 | 11/2003 |
| WO | WO 2005/049125 A1 | 6/2005 |
| WO | WO 2005/074819 A1 | 8/2005 |

* cited by examiner

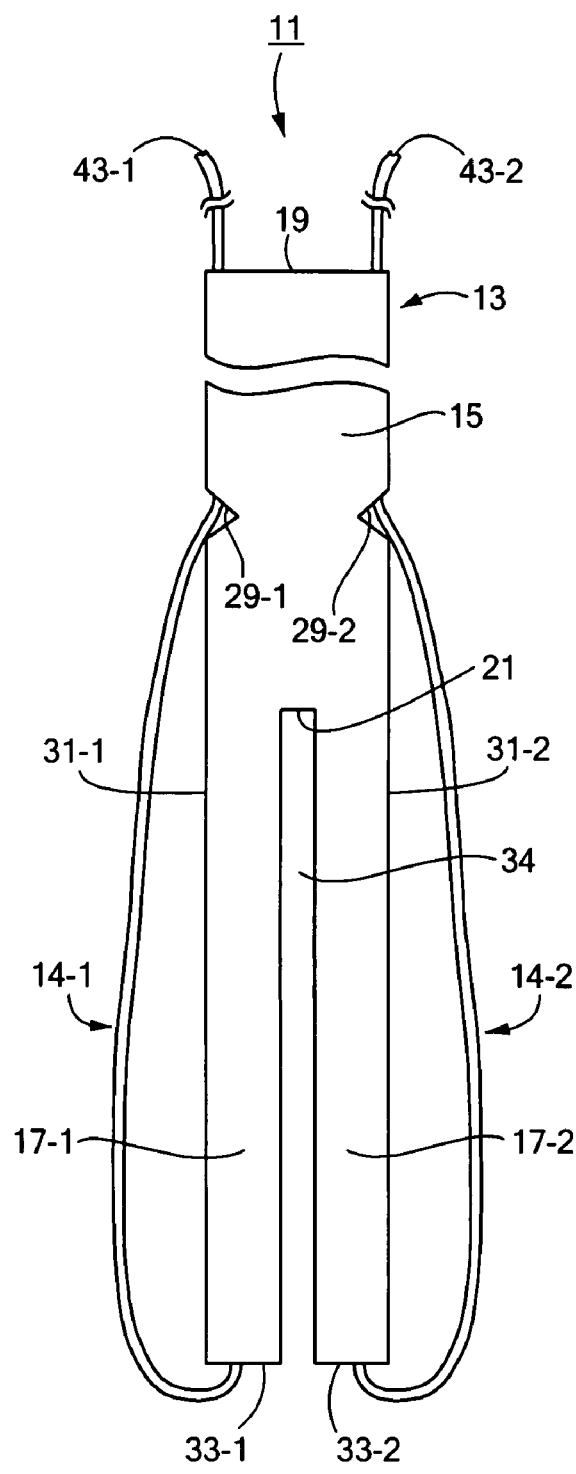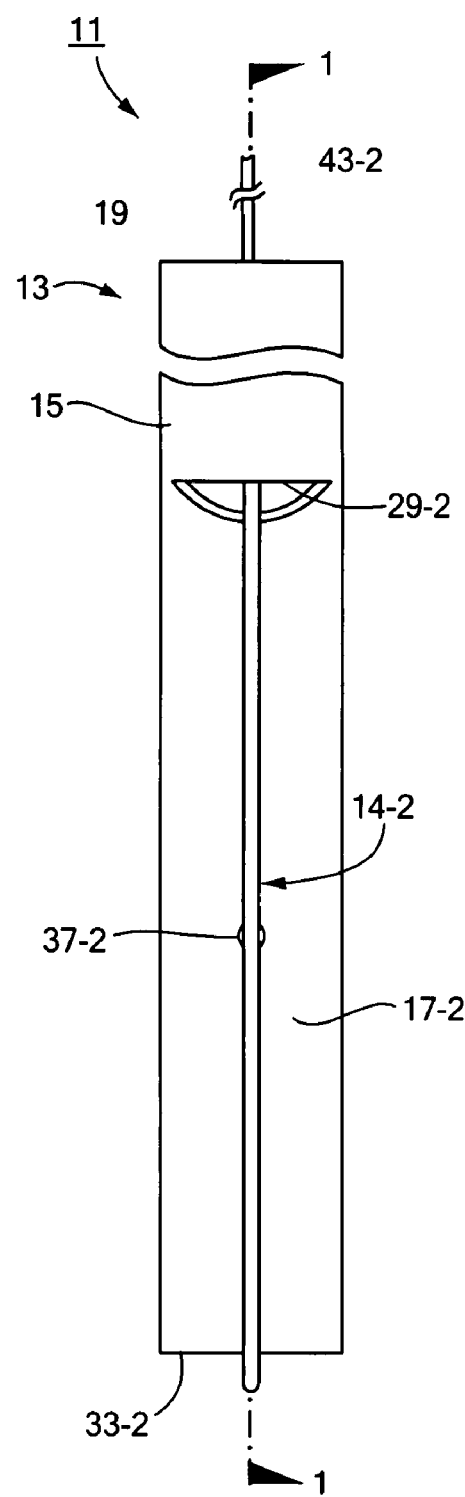
FIG. 1        FIG. 2

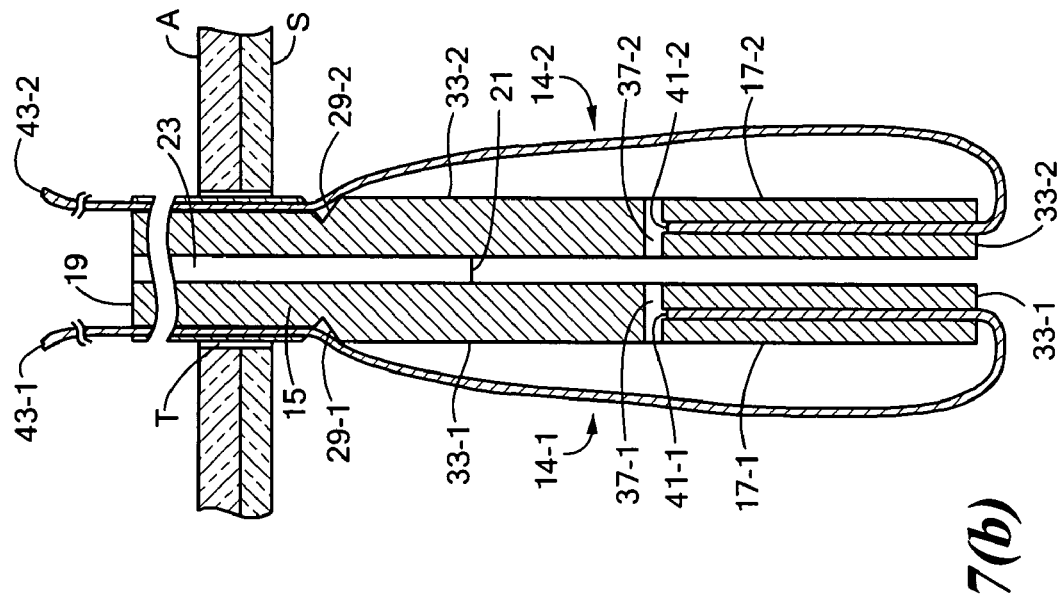
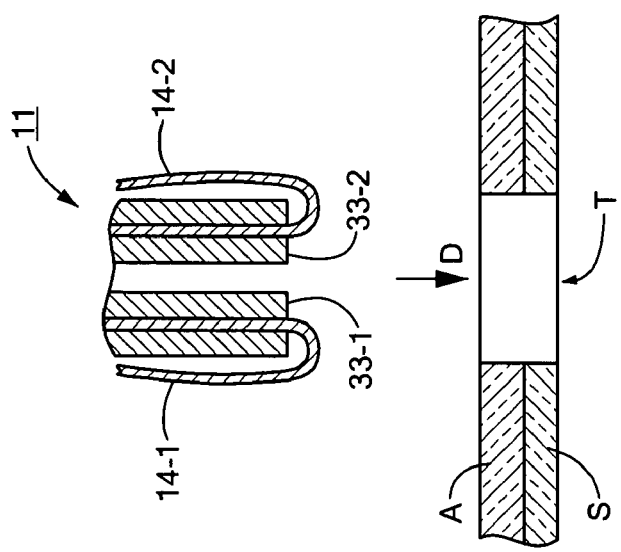
FIG. 7(b)
FIG. 7(a)

CATHETER ASSEMBLY INCLUDING FOLDABLE INTERNAL BOLSTER

BACKGROUND OF THE INVENTION

The present invention relates generally to medical catheters and relates more particularly to medical catheters of the type having an internal bolster disposed at one end of said medical catheter for retaining said end of said medical catheter within a patient.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside of the patient.

Although gastrostomies were first performed surgically, most gastrostomies are now performed using percutaneous endoscopy and result in the implantation in the patient of a feeding tube having a resilient dome-shaped member disposed at the internal end thereof to serve as an internal bolster (said feeding tube/internal bolster assembly also commonly referred to as a percutaneous endoscopic gastrostomy (PEG) device). Two of the more common percutaneous endoscopic techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

Although PEG devices of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. In addition, PEG devices of the type described above have a tendency to become worn after long periods of use. Consequently, a variety of replacement tube assemblies (also referred to in the art as replacement PEG devices) have been designed for implantation within the stoma tract following the removal of an initially-implanted PEG device. Examples of such devices are disclosed in U.S. Pat. No. 4,944,732, inventor Russo, which issued Jul. 31, 1990, and U.S. Pat. No. 5,836,924, inventors Kelliher et al., which issued Nov. 17, 1998, both of which are incorporated herein by reference.

Other patents and patent applications of interest include U.S. Pat. No. 4,863,438, inventors Gauderer et al., which issued Sep. 5, 1989; U.S. Pat. No. 5,720,734, inventors Copenhaver et al., which issued Feb. 24, 1998; U.S. Pat. No. 6,042,577, inventors Chu et al., which issued Mar. 28, 2000; and International Publication Number WO 03/092780A2, published Nov. 13, 2003, all of which are incorporated herein by reference.

SUMMARY OF THE INVENTION

According to one embodiment of the present invention, there is provided a catheter assembly comprising (a) a catheter, said catheter comprising (i) a tubular body having a proximal end, a distal end, a longitudinal lumen and a first bore, and (ii) a first flexible leg, said first flexible leg having a fixed end and a free end, said fixed end being joined to said distal end of said tubular body; and (b) a first flexible filament having a first end and a second end, said first end being fixed to said first flexible leg, said second end being slidably inserted through said first bore for use in drawing said free end of said first flexible leg towards said tubular body to form a first loop.

According to an alternate embodiment, the catheter assembly includes a catheter and a plurality of flexible filaments. The catheter includes a tubular body and a corresponding plurality of flexible legs. The tubular body is a generally hollow member shaped to include a proximal end, a distal end, a longitudinal lumen, a corresponding plurality of external notches, and a corresponding plurality of bores each extending from the proximal end to one of the notches. Each of the flexible legs has a fixed end and a free end, the fixed end being integrally formed on the distal end of the tubular body. One end of each flexible filament is fixed to one of the flexible legs, and the opposite end of the flexible filament is slidably inserted up through one of the bores. Consequently, by continued pulling of the filaments up through their respective bores, the free ends of the legs may be drawn towards the tubular body to form a plurality of loops suitable for use as an internal bolster.

For purposes of the present specification and claims, various relational terms like "top," "bottom," "up," "down," "proximal" and "distal" are used to describe the present invention when said invention is positioned in or viewed from a given orientation. It is to be understood that, by altering the orientation of the invention, certain relational terms may need to be adjusted accordingly.

Additional embodiments of the present invention will be set forth in part in the description which follows. In the description, reference is made to the accompanying drawings which form a part thereof and in which is shown by way of illustration certain embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various alternate embodiments of the invention:

FIG. 1 is a fragmentary front view of a first embodiment of a catheter assembly constructed according to the teachings of the present invention;

FIG. 2 is a fragmentary side view of the catheter assembly shown in FIG. 1;

FIG. 7(a) through 7(c) are fragmentary section views, illustrating a manner in which the catheter assembly of FIG. 1 may be implanted in a patient;

DETAILED DESCRIPTION OF PREFERRED EMBODIMENTS

Figure 3:
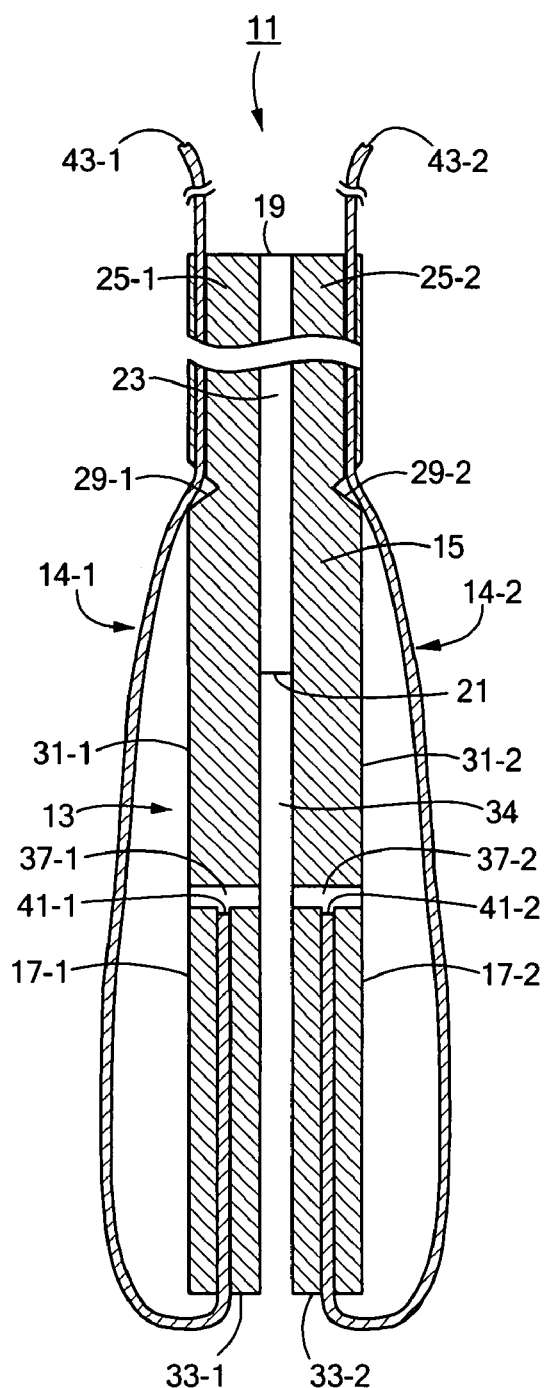
FIG. 3 is a fragmentary longitudinal section view of the catheter assembly of FIG. 2 taken along line 1-1.
Figure 4:
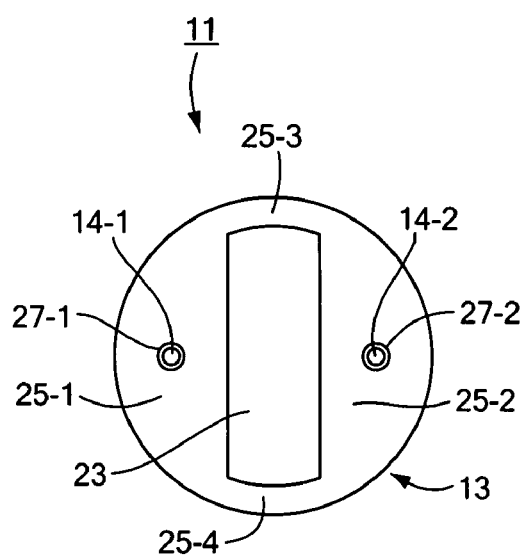
FIG. 4 is an enlarged top view of the catheter assembly shown in FIG. 1.
Figure 5:
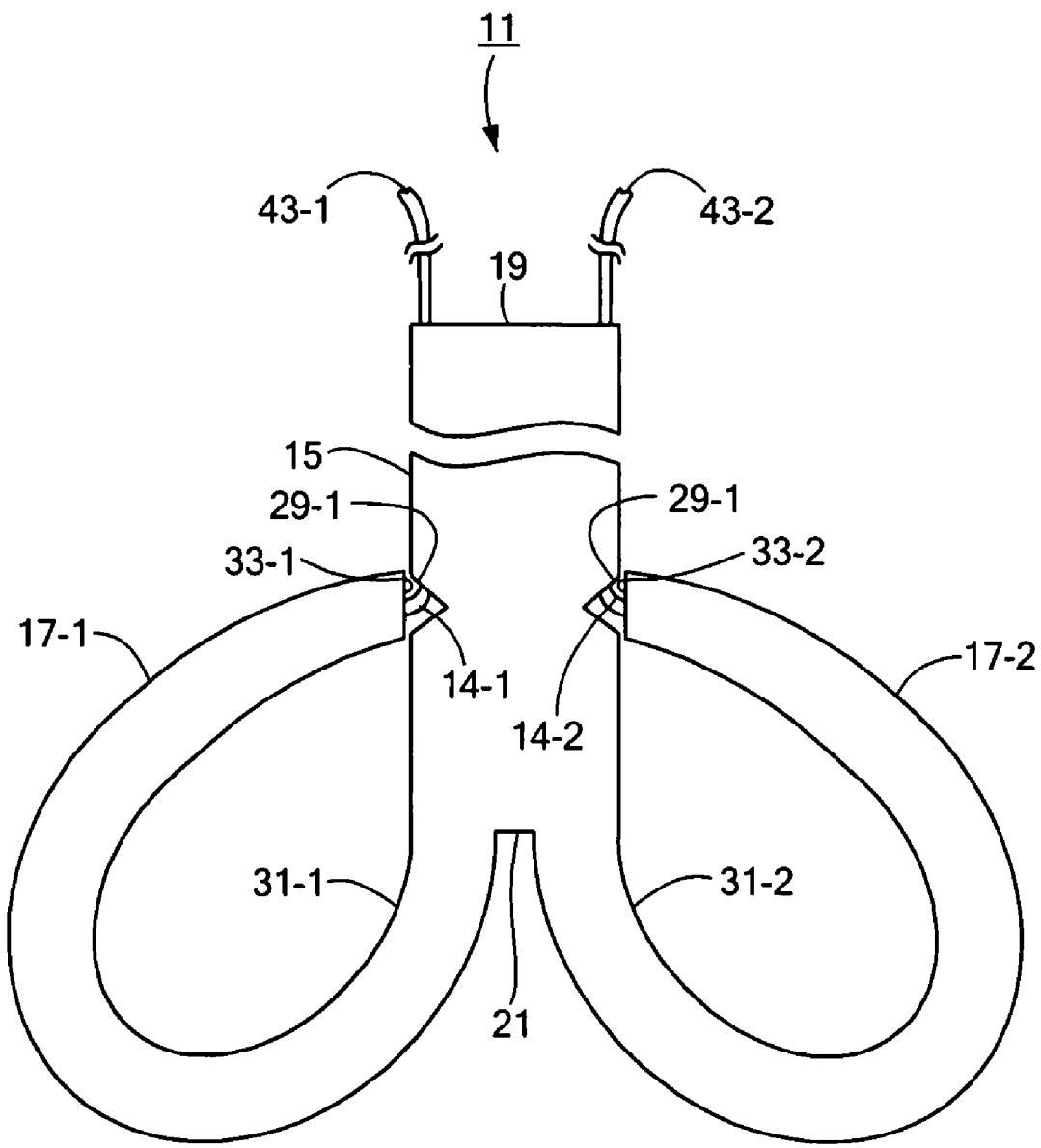
FIG. 5 is a fragmentary front view of the catheter assembly of FIG. 1.

Referring now to FIGS. 1 through 5, there are shown various views of a first embodiment of a catheter assembly constructed according to the teachings of the present invention, said catheter assembly being represented generally by reference numeral 11.

Catheter assembly 11 includes a medical catheter 13 and a pair of filaments 14-1 and 14-2.

Figure 6:
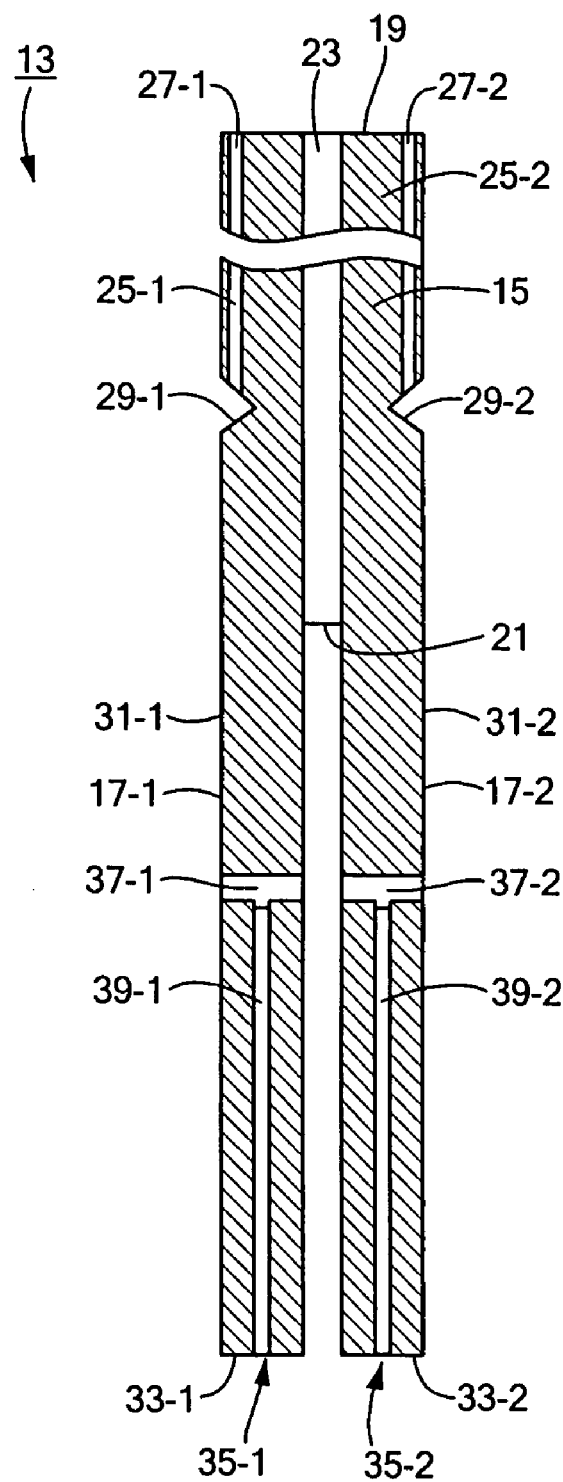
FIG. 6 is a fragmentary longitudinal section view of the catheter shown in FIG. 3.

Catheter 13, which is also shown separately in FIG. 6, is an elongated, unitary structure preferably made of a flexible, biocompatible material, such as molded silicone rubber. Catheter 13 is shaped to include a tubular body 15 and a pair of legs 17-1 and 17-2, legs 17-1 and 17-2 extending distally from body 15.

Body 15 comprises a generally hollow member shaped to include a proximal end 19, a distal end 21, and a longitudinal lumen 23 extending between proximal end 19 and distal end 21. Lumen 23, which may be generally rectangular in transverse cross-section and is designed to convey food and/or medications to a patient in need thereof, is positioned along the longitudinal axis of body 15 and is surrounded by walls 25-1 and 25-2 of comparatively greater transverse cross-sectional thickness and walls 25-3 and 25-4 of comparatively lesser transverse cross-sectional thickness. A first bore 27-1 is provided in wall 25-1 and may have a generally circular transverse cross-section, bore 27-1 extending generally longitudinally from proximal end 19 to an external notch 29-1 positioned at a point intermediate to proximal end 19 and distal end 21. A second bore 27-2 is provided in wall 25-2 and may have a generally circular transverse cross-section, bore 27-2 extending generally longitudinally from proximal end 19 to an external notch 29-2 positioned at a point intermediate to proximal end 19 and distal end 21. For reasons to be discussed further below, first bore 27-1 slidably receives filament 14-1, and second bore 27-2 slidably receives filament 14-2.

Legs 17-1 and 17-2, which may be generally semi-cylindrical in shape, are flexible members having fixed ends 31-1 and 31-2, respectively, that are integrally joined to distal end 21 of body 15 and free ends 33-1 and 33-2, respectively, that are disposed distal to body 15. Legs 17-1 and 17-2 are spaced apart from one another by a longitudinal opening 34, opening 34 being aligned with lumen 23 of body 15. A first cavity 35-1 is provided in leg 17-1, cavity 35-1 having a first portion 37-1 and a second portion 39-1, first portion 37-1 extending transversely across leg 17-1 at a point intermediate to fixed end 31-1 and free end 33-1, second portion 39-1 extending generally longitudinally from first portion 37-1 to free end 33-1. A second cavity 35-2 is provided in leg 17-2, cavity 35-2 having a first portion 37-2 and a second portion 39-2, first portion 37-2 extending transversely across leg 17-2 at a point intermediate to fixed end 31-2 and free end 33-2, second portion 39-2 extending generally longitudinally from first portion 37-2 to free end 33-2.

Filaments 14-1 and 14-2 are flexible members and may comprise a suitable polymer or metal and may further comprise a coating. For example, filaments 14-1 and 14-2 may be lengths of metal wire, either coated in plastic or uncoated. A first end 41-1 of filament 14-1 may be secured by an interference fit within second portion 39-1 of cavity 35-1, and a second end 43-1 of filament 14-1 may be slidably inserted in a proximal direction up through bore 27-1, with an intermediate portion of filament 14-1 forming a relaxed loop between free end 33-1 of leg 17-1 and notch 29-1. Similarly, a first end 41-2 of filament 14-2 may be secured by an interference fit within second portion 39-2 of cavity 35-2, and a second end 43-2 of filament 14-2 may be slidably inserted in a proximal direction up through bore 27-2, with an intermediate portion of filament 14-2 forming a relaxed loop between free end 33-2 of leg 17-2 and notch 29-2. (Instead of securing filaments 14-1 and 14-2 to legs 17-1 and 17-2, respectively, in the fashion described above, one could secure filaments 14-1 and 14-2 to legs 17-1 and 17-2, respectively, by arrangements including, but not limited to, putting a larger diameter at the ends of the filaments, tying filaments to the legs, looping the filaments through holes in the legs, choosing filaments which can melt into the legs, attaching something like a tag to the distal end of the filaments, etc.) As seen best in FIG. 5, when second ends 43-1 and 43-2 of filaments 14-1 and 14-2, respectively, are pulled proximally relative to proximal end 19 of catheter 13, free ends 33-1 and 33-2 are drawn towards notches 29-1 and 29-2, respectively, thereby causing legs 17-1 and 17-2 to be folded into opposing loops that are adapted to serve as an internal bolster. It should be understood that, although legs 17-1 and 17-2 fold in planar manner, the present invention encompasses embodiments in which the legs do not fold in a planar manner. For example, one leg could be looped over the other leg.

It should also be understood that, instead of securing first ends 41-1 and 41-2 of filaments 14-1 and 14-2, respectively, to legs 17-1 and 17-2, respectively, by an interference fit, one could insert-mold legs 17-1 and 17-2 around first ends 41-1 and 41-2, respectively.

Figure 7C:
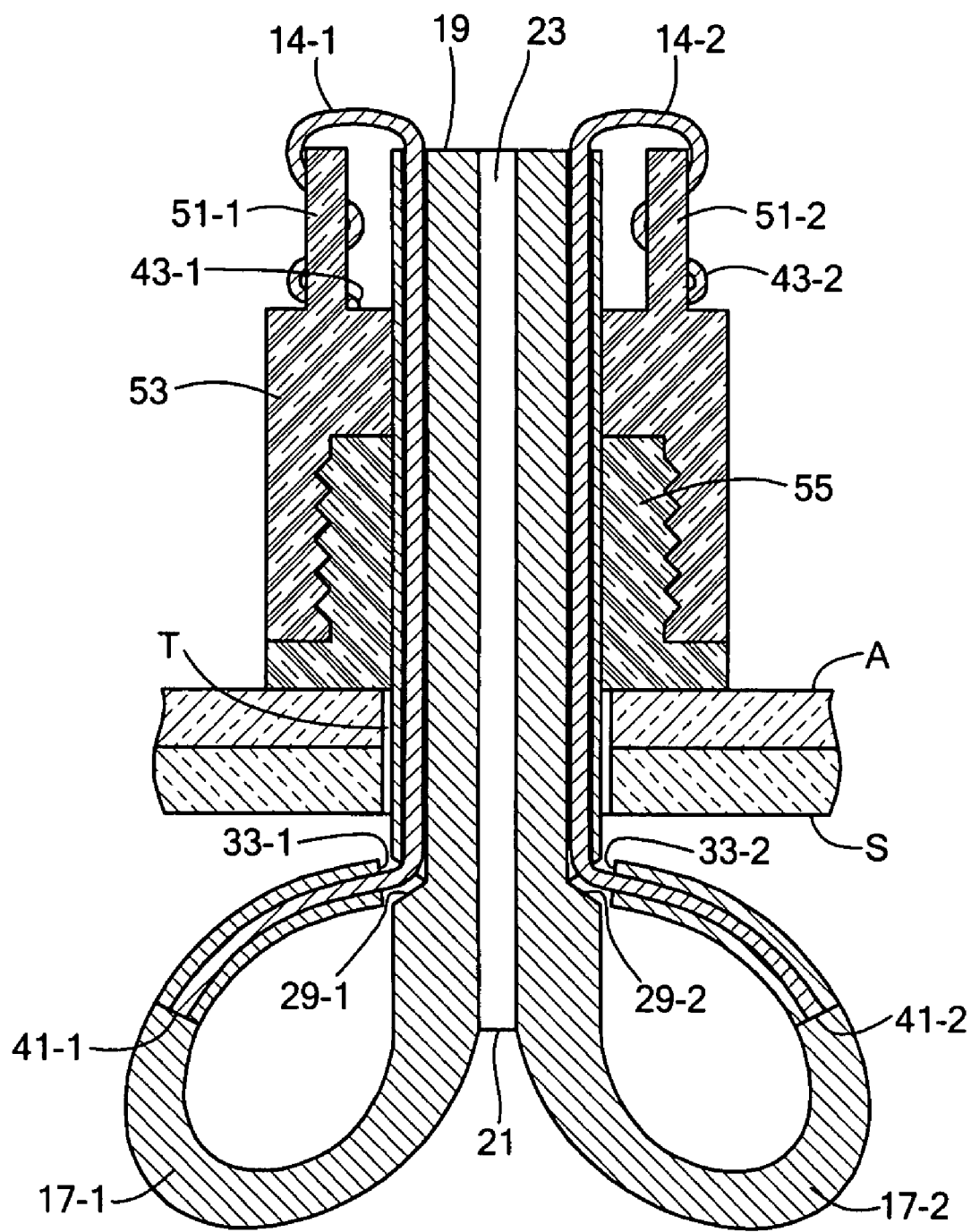

Referring now to FIGS. 7(a) through 7(c), there is schematically shown a manner in which catheter assembly 11 may be implanted in a patient. (For illustrative purposes, catheter assembly 11 is shown herein as a replacement PEG device implanted in the stomach of a patient; however, it is to be understood that catheter assembly 11 may be used either as a replacement device or as an initial placement device and may be implanted in locations within a patient, other than the stomach, where the delivery and/or drainage of fluids is desirable (e.g., intravenous catheters, drainage catheters, access ports, etc.).) First, referring to FIG. 7(a), there is shown the distal end of assembly 11 being inserted in the direction indicated by arrow D down towards a stoma tract T that has been established between the abdominal wall A and the stomach wall S of a patient. As can be seen, catheter 13 is appropriately sized so that it may be inserted easily through stoma tract T. If desired, the distal end of assembly 11 could be introduced into the patient with or through a sheath to cover filaments 14-1 and 14-2. In addition, the body may be grooved to hide filaments 14-1 and 14-2.

Next, as seen in FIG. 7(*b*), assembly 11 is inserted into the patient to the extent required, with notches 29-1 and 29-2 positioned within the patient's stomach and proximal end 19 of catheter 13 and ends 43-1 and 43-2 of filaments 14-1 and 14-2, respectively, extending externally relative to the patient. It should be noted that, during such placement of assembly 11 in stoma tract T, legs 17-1 and 17-2 are not in a looped state, but rather, extend substantially along the longitudinal axis of body 15.

Next, as seen in FIG. 7(*c*), filaments 14-1 and 14-2 are drawn proximally, causing free ends 33-1 and 33-2 of legs 17-1 and 17-2, respectively, to be drawn towards notches 29-1 and 29-2, respectively, in such a way as to form a pair of opposed loops. As can be seen, such loops are adapted to engage the bottom of stomach wall S and, thereby, serve to prevent the withdrawal of the distal end of assembly 11 from the patient. To facilitate the aforementioned proximal drawing of filaments 14-1 and 14-2 and to permit the retention of filaments 14-1 and 14-2 in such a proximally drawn state, ends 43-1 and 43-2 of filaments 14-1 and 14-2, respectively, may be secured to a pair of posts 51-1 and 51-2 provided on a cap 53. Cap 53 may then be screwed onto an external bolster 55, external bolster 55 being inserted over catheter 13. In this manner, the screwing of cap 53 onto bolster 55 causes the tensioning of filaments 14-1 and 14-2 and, as a result, the bending of legs 17-1 and 17-2, respectively, into loops. However, it should be noted that the foregoing arrangement is merely one way of securing filaments 14-1 and 14-2 and looped legs 17-1 and 17-2, there being many other ways. For example, the proximal ends of the filaments could be tied through a hole in the proximal end of the tubular body. Instead of posts, one could secure the filaments to the body or to each other. The proximal ends of the filaments could have an additional tag, ball or increased diameter which could snap into posts, tubular body or another mechanism. If filaments were secured into a cap, the twisting of the cap could pull the filaments proximally and cause the legs to loop upwards.

With assembly 11 thus implanted, food and/or medications may be delivered to the patient by inserting a suitable fitting into the proximal end of lumen 23.

To remove assembly 11 from the patient, the proximal tensioning of filaments 14-1 and 14-2 is released, for example, by unscrewing cap 53 from bolster 55. With such tensioning removed, legs 17-1 and 17-2 straighten, thereby permitting assembly 11 to be withdrawn through stoma tract T.

As can readily be appreciated, assembly 11 can be repeatedly transformed between a state in which legs 17-1 and 17-2 are looped and a state in which legs 17-1 and 17-2 are straightened.

Figure 8:
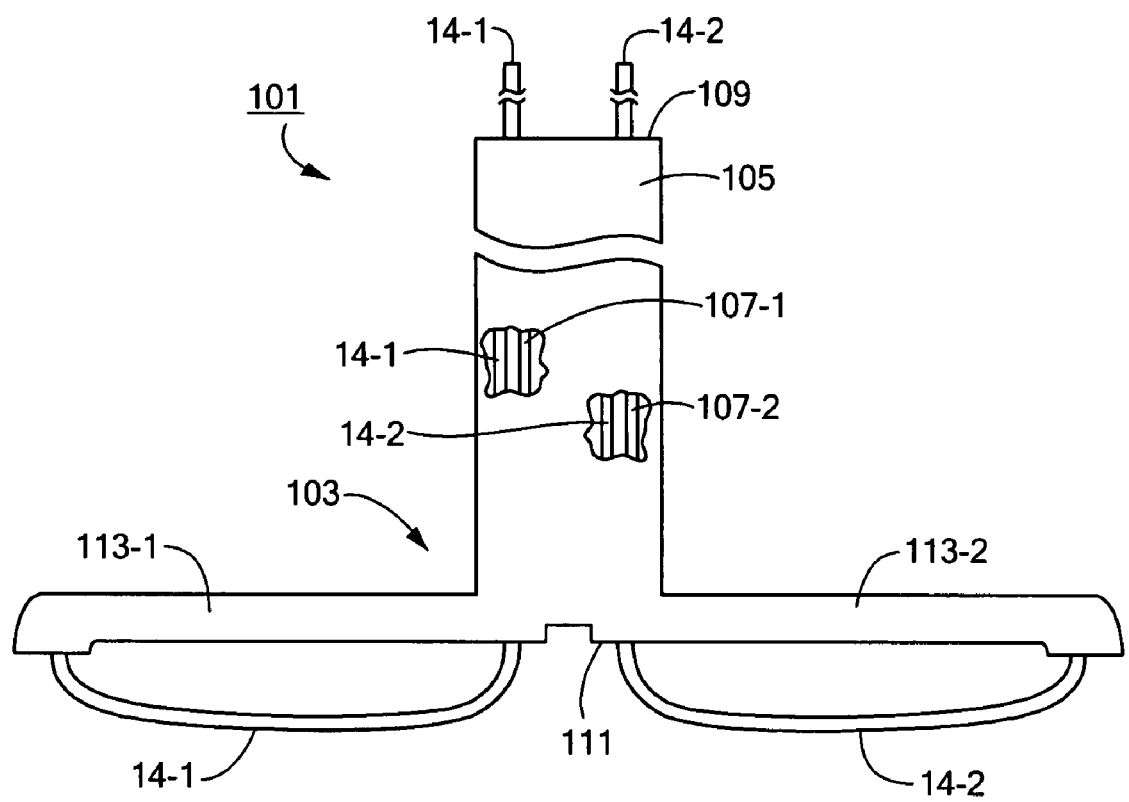
FIG. 8 is a fragmentary front view, broken away in part, of a second embodiment of a catheter assembly constructed according to the teachings of the present invention.
Figure 9:
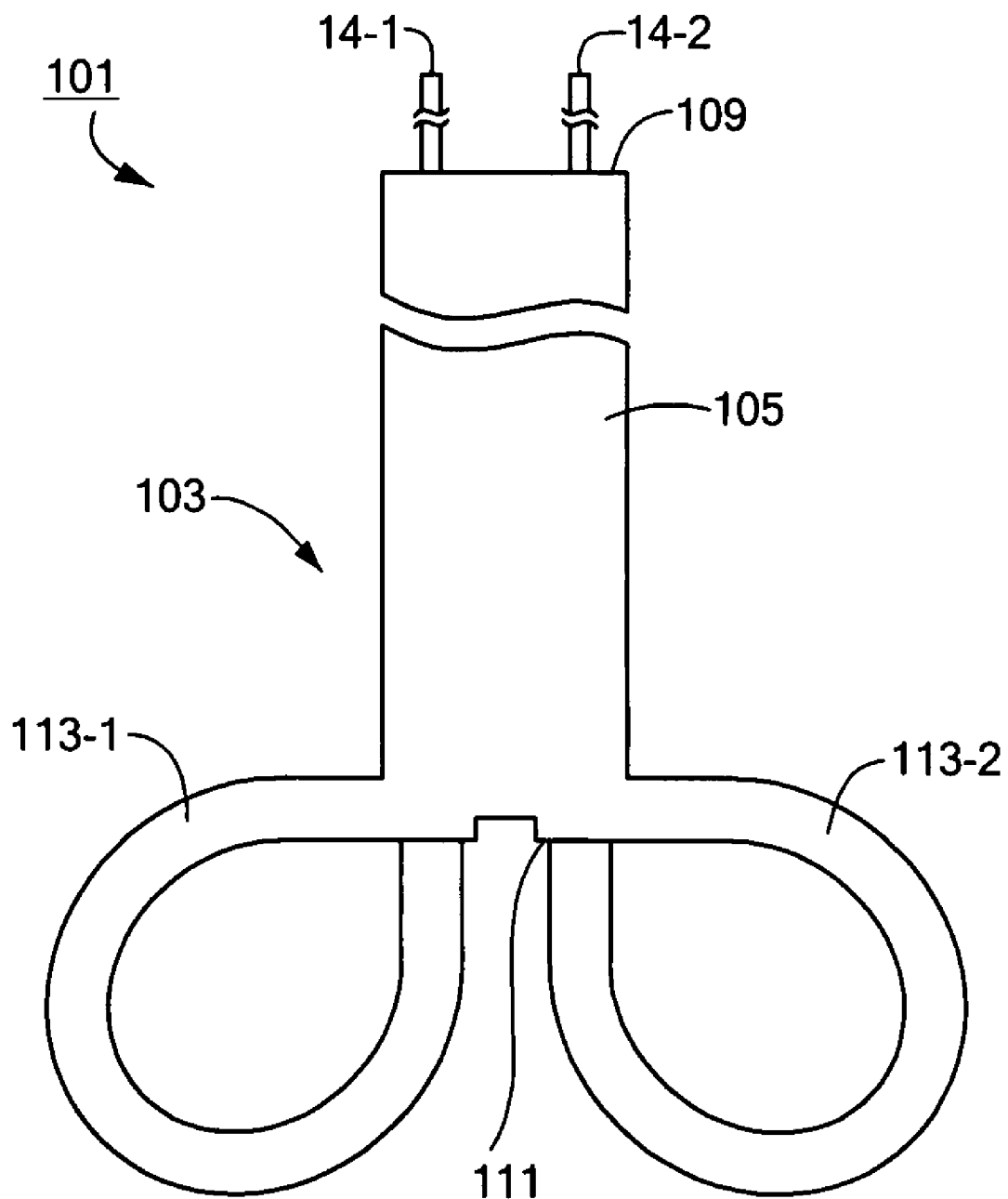
FIG. 9 is a fragmentary front view of the catheter assembly of FIG. 8.

Referring now to FIGS. 8 and 9, there are shown front views of a second embodiment of a catheter assembly constructed according to the teachings of the present invention, said catheter assembly being represented generally by reference numeral 101.

Assembly 101 is similar in many respects to assembly 11, the principal differences between the two assemblies being that assembly 101 includes a medical catheter 103, instead of catheter 13. Catheter 103 differs principally from catheter 101 in that catheter 103 includes (i) a body 105 having a pair of longitudinal bores 107-1 and 107-2 that extend from the proximal end 109 of body 105 to the distal end 111 of body; and (ii) a pair of flexible legs 113-1 and 113-2 that, in an unfolded state, extend generally perpendicularly relative to body 105 and that, when folded, loop in a manner that is flipped relative to legs 17-1 and 17-2 of assembly 11.

It should be understood that, although each of assembly 11 and assembly 101 includes two legs that are bent into two loops, the present invention encompasses embodiments that include more than two legs bent into a corresponding number of loops. Also, it should be understood that, although the each of the legs of assemblies 11 and 101 is operated by its own filament, the invention encompasses arrangements in which one filament is used to operate both legs (e.g., the filament is looped through both legs, the filament is looped through one leg and tied to the other leg, the filament has split ends, etc.).

In addition, it should be understood that the catheter assemblies of the present invention are not limited to use as PEG devices and may be used in other situations where catheters may need to be temporarily or permanently secured within a patient, such as in the case of intravenous catheters, drainage catheters, access ports, etc.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A catheter assembly comprising:
   (a) a catheter, said catheter comprising
      (i) a tubular body having a proximal end, a distal end, a longitudinal lumen and a first bore, wherein said first bore extends generally parallel to said longitudinal lumen, and
      (ii) a first flexible leg, said first flexible leg having a fixed end, a free end, and a first cavity, said first cavity extending from said free end towards said fixed end, said fixed end being joined to said distal end of said tubular body; and
   (b) a first flexible filament having a first end and a second end, said first end being inserted into said first cavity through said free end and securely retained within said first flexible leg, said second end being slidably inserted through said first bore for use in drawing said free end of said first flexible leg towards said tubular body to form a first loop.

2. The catheter assembly as claimed in claim 1 wherein said catheter further comprises a second bore and a second flexible leg, said second flexible leg having a fixed end and a free end, said fixed end of said second flexible leg being joined to said distal end of said tubular body, said catheter assembly further comprising a second flexible filament having a first end and a second end, said first end of said second flexible filament being fixed to said second flexible leg, said second end of said second flexible filament being slidably inserted through said second bore for use in drawing said free end of said second flexible leg towards said tubular body to form a second loop.

3. The catheter assembly as claimed in claim 2 wherein said tubular body and said first and second flexible legs form a unitary structure.

4. The catheter assembly as claimed in claim 2 wherein said first flexible leg and said second flexible leg are separated by a space, said space being aligned with said longitudinal lumen of said tubular body.

5. The catheter assembly as claimed in claim 1 wherein said tubular body further comprises a first opening disposed at a point intermediate to said proximal end and said distal end, said first bore extending generally longitudinally from said proximal end of said tubular body to said first opening.

6. The catheter assembly as claimed in claim 2 wherein said tubular body further comprises a pair of openings disposed between said proximal end and said distal end, said first bore extending generally longitudinally from said proximal end of said tubular body to one of said openings, said second bore extending generally longitudinally from said proximal end of said tubular body to the other of said openings.

7. The catheter assembly as claimed in claim 2 wherein said second flexible leg has a second cavity extending from said free end towards said fixed end, said first end of said second filament being inserted into said second cavity through said free end of said second flexible leg and securely retained therewithin.

8. The catheter assembly as claimed in claim 1 wherein said catheter assembly is a PEG device.

9. The catheter assembly as claimed in claim 1 wherein said first flexible leg, when not drawn towards said tubular body to form a loop, extends generally parallel to said tubular body.

10. The catheter assembly as claimed in claim 1 wherein said first flexible leg, when not drawn towards said tubular body to form a loop, extends generally perpendicular to said tubular body.

11. The catheter assembly as claimed in claim 1 wherein said first bore extends the length of said tubular body.

12. A catheter assembly comprising:
(a) a tubular body having a proximal end, a distal end, a longitudinal lumen and a bore, wherein said bore extends generally parallel to said longitudinal lumen,
(b) a flexible leg, said flexible leg having a fixed end and a free end, said fixed end being joined to said distal end of said tubular body; and
(c) a flexible filament having a first end and a second end, said first end being fixed to said flexible leg, said second end being slidably inserted through said bore for use in drawing said free end of said flexible leg towards said tubular body to form a loop;
(d) wherein said flexible leg has a cavity extending from said free end towards said fixed end, said first end of said flexible filament being inserted into said cavity through said free end and securely retained therewithin.

13. The catheter assembly as claimed in claim 12 wherein said flexible leg, when not drawn towards said tubular body to form a loop, extends generally parallel to said tubular body.

14. The catheter assembly as claimed in claim 12 wherein said flexible leg, when not drawn towards said tubular body to form a loop, extends generally perpendicular to said tubular body.

15. A catheter assembly comprising:
(a) a tubular body having a proximal end, a distal end, and a longitudinal lumen,
(b) a plurality of flexible legs, each of said flexible legs having a fixed end, a free end, and a cavity, said fixed end of each of said flexible legs being joined to said distal end of said tubular body; and
(c) means for drawing said free ends of said flexible legs towards said tubular body to form loops, wherein said drawing means comprises a plurality of filaments, one of each of said plurality of filaments being inserted into and securely retained within the cavity of a corresponding one of said plurality of flexible legs.

16. The catheter assembly as claimed in claim 15 wherein each of said plurality of filaments comprises and end fixed within a corresponding one of said plurality of flexible legs.

17. The catheter assembly as claimed in claim 1 further comprising a cap, the first end of the first flexible filament being secured to the cap.

18. The catheter assembly as claimed in claim 17 further comprising an external bolster, the external bolster being inserted over the proximal end of the tubular body.

19. The catheter assembly as claimed in claim 18 wherein the cap is threadingly engageable with the external bolster.

20. A catheter assembly comprising:
(a) a catheter, said catheter comprising:
(i) a tubular body, the tubular body having a proximal end, a distal end, a longitudinal lumen, a first bore and a second bore, the first bore extending generally longitudinally from the proximal end to a first external notch positioned intermediate to the proximal end and the distal end, the second bore extending generally longitudinally from the proximal end to a second external notch positioned intermediate to the proximal end and the distal end,
(ii) a first flexible leg, said first flexible leg having a fixed end, a free end, and a cavity, said fixed end being joined to said distal end of said tubular body, and
(iii) a second flexible leg, said second flexible leg having a fixed end, a free end, and a cavity, said fixed end being joined to said distal end of said tubular body;
(b) a first flexible filament having a first end and a second end, said first end of said first flexible filament being inserted into and securely retained within the cavity of said first flexible leg, said second end of said first flexible filament being slidably inserted through said first notch and said first bore for use in drawing said free end of said first flexible leg towards said tubular body to form a first loop; and
(c) a second flexible filament having a first end and a second end, said first end of said second flexible filament being inserted into and securely retained within the cavity of said second flexible leg, said second end of said second flexible filament being slidably inserted through said second notch and said second bore for use in drawing said free end of said second flexible leg towards said tubular body to form a second loop.

21. The catheter assembly as claimed in claim 20 wherein an intermediate portion of said first flexible filament extends distally from said free end of said first flexible leg.

* * * * *